US011351100B2

(12) United States Patent
Mukai et al.

(10) Patent No.: US 11,351,100 B2
(45) Date of Patent: Jun. 7, 2022

(54) HAIR COLORING AGENT COMPOSITION

(71) Applicant: SUNNYPLACE CO., LTD., Tokyo (JP)

(72) Inventors: Nobuhito Mukai, Taito-ku (JP); Takashi Mukai, Taito-ku (JP)

(73) Assignee: SUNNYPLACE CO., LTD., Tokyo (JP)

( * ) Notice: Subject to any disclaimer, the term of this patent is extended or adjusted under 35 U.S.C. 154(b) by 0 days.

(21) Appl. No.: 17/286,381

(22) PCT Filed: Dec. 18, 2018

(86) PCT No.: PCT/JP2018/046638
§ 371 (c)(1),
(2) Date: Apr. 16, 2021

(87) PCT Pub. No.: WO2020/079857
PCT Pub. Date: Apr. 23, 2020

(65) Prior Publication Data
US 2021/0346267 A1 Nov. 11, 2021

(30) Foreign Application Priority Data
Oct. 18, 2018 (JP) .............................. JP2018-197009

(51) Int. Cl.
*A61Q 5/10* (2006.01)
*A61K 8/49* (2006.01)
*A61K 8/20* (2006.01)
*A61K 8/41* (2006.01)
*A61K 8/44* (2006.01)
*A61K 8/46* (2006.01)

(52) U.S. Cl.
CPC .............. *A61K 8/4946* (2013.01); *A61K 8/20* (2013.01); *A61K 8/416* (2013.01); *A61K 8/44* (2013.01); *A61K 8/46* (2013.01); *A61Q 5/10* (2013.01)

(58) Field of Classification Search
CPC ........ A61Q 5/10; A61Q 5/06; A61K 2800/43; A61K 8/416; A61K 2800/432; A61K 8/44; A61K 8/41; A61K 8/42; A61K 2800/5426; A61K 8/92; A61K 2800/48; A61K 8/442
USPC .......................................................... 8/426
See application file for complete search history.

(56) References Cited

U.S. PATENT DOCUMENTS

2012/0110750 A1* 5/2012 Cremer ................. C09B 69/109
8/402
2017/0143608 A1* 5/2017 Saeki ...................... A61Q 19/02
2017/0181946 A1* 6/2017 Manneck ................. A61K 8/44

FOREIGN PATENT DOCUMENTS

JP H11-501947 2/1999
JP 2012-171952 9/2012
(Continued)

OTHER PUBLICATIONS

Search Report and Written Opinion received in International Application No. PCT/JP2018/046638; dated Mar. 3, 2019.

*Primary Examiner* — Eisa B Elhilo
(74) *Attorney, Agent, or Firm* — ALG Intellectual Property, LLC

(57) ABSTRACT

A hair coloring composition may include at least one selected from the group consisting of thioglycolic acid, cysteine, 3-mercapto-1,2 - propanediol, cysteamine, derivatives and salts thereof, and a basic dye, a HC dye, an amino (Continued)

acid, cationic surfactant, thickener, oil agent, pH adjuster, and wetting agent, wherein the pH of the hair coloring agent composition is 3.5 or higher.

8 Claims, 3 Drawing Sheets

(56) References Cited

FOREIGN PATENT DOCUMENTS

| | | |
|---|---|---|
| JP | 2017-31085 | 2/2017 |
| JP | 2017-031085 A * | 2/2017 |
| JP | 2017-88502 | 5/2017 |
| WO | WO-2016/166201 | 10/2016 |

* cited by examiner

[Figure 1]

| | Display name | Molecular weight | INCI name | 3-mercapto-1,2-propanediol 0% | 3-mercapto-1,2-propanediol 1% | 3-mercapto-1,2-propanediol 3% |
|---|---|---|---|---|---|---|
| basic | Red51 | 279.775 | Basic Red 51 | | | |
| | Brown16 | 356.857 | Basic Brown 16 | | | |
| | Brown17 | 401.854 | Basic Brown 17 | | | |
| | Blue75 | 516.177 | Basic Blue 75 | | | |
| | Blue77 | 495.337 | Basic Blue 77 | | | |
| | Blue99 | 451.752 | Basic Blue 99 | | | |
| | Violet2 | 365.91 | Basic Violet 2 | | | |
| | Yellow57 | 371.872 | Basic Yellow 57 | | | |

[Figure 2]
| | | |
|---|---|---|
| a) | 3-mercapto-1,2-propanediol 0% Formulation<br>Basic Brown 16 0.2%, Basic Blue 77 0.2% | 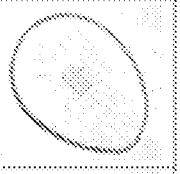 |
| b) | 3-mercapto-1,2-propanediol 0.5% Formulation<br>Basic Brown 16 0.2%, Basic Blue 77 0.2% | 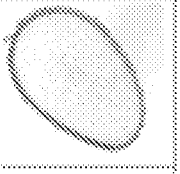 |
| c) | 3-mercapto-1,2-propanediol 1.0% Formulation<br>Basic Brown 16 0.2%, Basic Blue 77 0.2% | 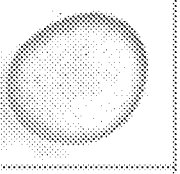 |
| d) | 3-mercapto-1,2-propanediol 3.0% Formulation<br>Basic Brown 16 0.2%, Basic Blue 77 0.2% | 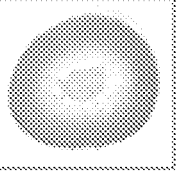 |

[Figure 3]
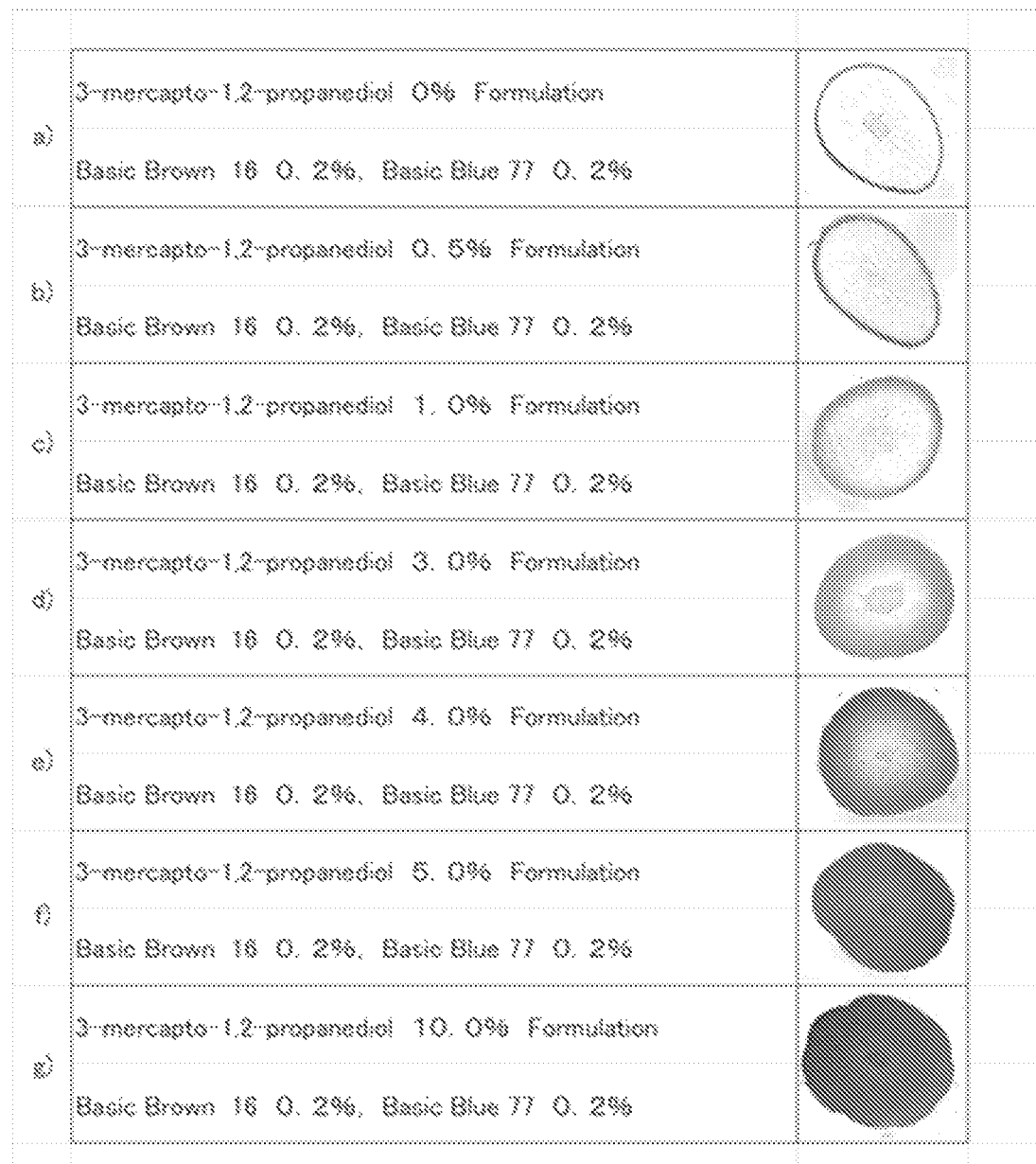

HAIR COLORING AGENT COMPOSITION

TECHNICAL FIELD

The present invention relates to a hair coloring agent composition, and more particularly relates to a hair coloring agent composition capable of reducing skin disorders.

BACKGROUND ART

Hair coloring mainly includes hair color, which is a permanent hair dye for quasi-drugs, and hair manicure and hair color treatment, which are semi-permanent hair dyes for cosmetics. In particular, the hair color of permanent hair dyes mainly contains a substance called para-phenylenediamine (oxidation dye), but in the case of dark black colors, the amount of diamine compounds is large, so further attention is needed.

For example, as a hair coloring composition containing para-phenylenediamine (oxidative dye), a hair coloring composition characterized by containing (a) water-soluble peroxygen bleach; (b) a bleaching aid which is selected from organic peroxyic acid bleach precursor and/or preformed organic peroxy acid; and (c) one or more hair coloring agents is known (Patent literature 1).

PRIOR ART LITERATURE

Patent Literature

Patent literature 1: JP-A1-H11-501947

DISCLOSURE OF THE INVENTION

Problems to be Resolved by the Invention

However, in the prior art including the above Patent literature 1, those containing para-phenylenediamine (oxidation dye) are further noted because the amount of the diamine-based compound is large in the case of a dark black color as described above. In recent years, skin disorders have been reported due to a substance called para-phenylenediamine (oxidative dye).

In addition, hair manicure, which is a semi-permanent hair dye, is characterized by the fact that the pigment (acid dye) penetrates into the inside of the hair with one use and has a color retention of 2 to 3 weeks, but, the longer it adheres to the scalp and the longer it is left, the more difficult it is to remove the dyed pigment. It is difficult to apply to the hairline on the side to be treated. Further, it is a hair dye that is often avoided in salons and beauty salons because it is not dyed as well as hair color for the skill of the practitioner.

Therefore, an object of the present invention is to provide a para-phenylenediamine-free hair coloring agent capable of reducing skin disorders.

Means of Solving the Problems

In order to achieve the above object, the present inventors have found the present invention as a result of diligent studies on hair color treatment.

That is, a hair coloring agent composition according to the present invention is characterized by comprising basic dye, HC dye, an amino acid, a cationic surfactant, a thickener, an oil agent, a pH adjusting agent, a wetting agent, and at least one selected from the group consisting of thioglycolic acid, cysteine, 3-mercapto-1,2-propanediol, cysteamine, and derivatives and salts thereof, wherein the pH of the hair coloring agent composition is pH 3.5 or higher.

Further, in a preferred embodiment of the hair coloring agent composition of the present invention, it is characterized in that the pH adjusting agent is at least one selected from citric acid, phosphoric acid, lactic acid, malic acid, aqueous ammonia, ammonium hydrogencarbonate, ammonium carbonate, potassium hydroxide, sodium hydroxide, monoethanolamine, ammonium phosphate, sodium citrate, ammonium citrate, sodium lactate, potassium phosphate, and sodium phosphate.

Further, in a preferred embodiment of the hair coloring agent composition of the present invention, it is characterized in that the amino acid is at least one selected from cysteine, arginine, lysine, histidine and salts thereof.

Further, in a preferred embodiment of the hair coloring agent composition of the present invention, it is characterized in that under the INCI (INCI: International Nomenclature of Cosmetic Ingredient) name, the basic dye is at least one selected from Basic Blue 3, Basic Blue 7, Basic Blue 9, Basic Blue 26, Basic Blue 75, Basic Blue 77, Basic Blue 99, Basic Blue 124, Basic Red 51, Basic Red 76, Basic Yellow 57, Basic Purple 2, Basic Brown 16 or basic brown 17.

Further, in a preferred embodiment of the hair coloring agent composition of the present invention, it is characterized in that under the INCI (International Nomenclature of Cosmetic Ingredient) name, the HC dye is at least one selected from HC blue 2, HC blue 12, HC blue 14, HC Blue 15, HC Blue 16, HC Blue 18, HC Yellow 2, HC Yellow 4, HC Yellow 5, HC Red 1, HC Red 3, or HC Orange 1.

Further, in a preferred embodiment of the hair coloring agent composition of the present invention, it is characterized in that the cationic surfactant is a quaternary ammonium salt and/or a tertiary amine.

Further, in a preferred embodiment of the hair coloring agent composition of the present invention, it is characterized in that the quaternary ammonium salt is an alkyltrimethylammonium chloride solution, stearyltrimethylammonium chloride, or stearyltrimethylammonium bromide.

Further, in a preferred embodiment of the hair coloring agent composition of the present invention, it is characterized in that the tertiary amine is dimethylaminopropyl amide stearate, diethyl aminoethyl amide stearate, or behenamide propyl dimethylamine.

Further, the hair coloring agent of the present invention is characterized by containing the hair coloring agent composition of the present invention.

Effect of Invention

According to the hair coloring agent composition of the present invention, it has the advantage effects that it does not contain para-phenylenediamine and is suitable for those who are suffering from scalp or who are worried about contact dermatitis. Further, it has the advantage effects that it is possible to provide a hair color product wherein it can be used with confidence and has good color retention because it has the potential to prolong the use of hair color due to aging. Further, it has the advantage effects that it is possible to provide a hair color product that can be applied to the new part without worrying about adhesion to the scalp even on the side of the treatment.

Further, according to the hair coloring agent composition of the present invention, it has the advantage effects that the permeability is good and the amount of dyeing agent or the like can be reduced by the use of a specific component.

BRIEF DESCRIPTION OF THE DRAWINGS

FIG. 1 shows the observation results by an optical microscope of hair cross-section samples treated in a 0%, 1%, and 3% solution of 3-mercapto-1,2-propanediol when various dyes were used.

FIG. 2 shows the observation results by an optical microscope of hair cross-section samples treated in a 0%, 0.5%, 1%, and 3% solution of 3-mercapto-1,2-propanediol when 0.2% of Basic Brown 16 and 0.2% of Basic Blue 77 were mixed to make a dark brown color.

FIG. 3 shows the observation results by an optical microscope of hair cross-section samples treated in a 0%, 0.5%, 1%, 3%, 4%, 5% and 10% solution of 3-mercapto-1,2-propanediol when 0.2% of Basic Brown 16 and 0.2% of Basic Blue 77 were mixed to make a dark brown color.

MODE FOR CARRYING OUT THE INVENTION

A hair coloring agent composition according to the present invention is characterized by comprising basic dye, HC dye, an amino acid, a cationic surfactant, a thickener, an oil agent, a pH adjusting agent, a wetting agent, and at least one selected from the group consisting of thioglycolic acid, cysteine, 3-mercapto-1,2-propanediol, cysteamine, and derivatives and salts thereof, wherein the pH of the hair coloring agent composition is pH 3.5 or higher. This is because the present inventors have found that a formulation of thioglycerin (scientific name: 3-mercapto-1,2-propanediol) makes it possible to obtain a good hair dyeing even if the pH is not raised or heated, as compared with the hair dyed by raising the pH and heating without adding thioglycerin or the like. Further, in the hair coloring agent composition of the present invention, it was found that the cuticle can be easily opened by setting the pH to 6.8 or higher, and at the same time, it was found that it is a product that can perform color treatment while sending basic amino acids such as L-arginine, L-lysine, L-histidine, and their salts into the hair to supplement and repair the basic amino acids that have flowed out due to pain. That is, although in hair color treatments and the like, cuticles (hair follicles) and cortex near the surface of the hair are dyed, and in some cases it is not possible to achieve a hair color having a sufficiently long-lasting color, when the hair coloring agent composition of the present invention is applied, it is possible to open the cuticle, and as a result, it has an advantageous effect that a hair color having a good long-lasting color can be achieved.

Further, in the present invention, the reason for selecting at least one selected from the group consisting of thioglycolic acid, cystine, 3-mercapto-1,2-propanediol, cysteamine, and derivatives and salts thereof is as follows. This is because, by including these components, components such as dyes can be deeply penetrated into the hair, and even a small amount of dye can sufficiently realize hair color. Moreover, this is because, by including these components, it is possible to maintain the effect of the dye for a long period of time. In the present invention, among thioglycolic acid, cystine, 3-mercapto-1,2-propanediol, cysteamine, and derivatives and salts thereof, 3-mercapto-1,2-propanediol can be preferably used from the viewpoint of odor and crystal precipitation etc.

In a preferred embodiment of the present invention, the content of at least one component selected from the group consisting of thioglycolic acid, cystine, 3-mercapto-1,2-propanediol, cysteamine, and derivatives and salts thereof may be 0.01 to 10.0% by weight, preferably 0.05 to 5.0% by weight, more preferably 0.1 to 3.0% by weight, to the total amount of the hair coloring agent, from the viewpoint of a composition that is hypoallergenic and has an excellent effect of promoting penetration into the hair.

Further, in a preferred embodiment of the hair coloring agent composition of the present invention, from the viewpoint of facilitating the opening of the cuticle and adjusting the pH to a desired value or higher, as the pH adjusting agent, mention may be made of at least one selected from citric acid, phosphoric acid, lactic acid, malic acid, aqueous ammonia, ammonium hydrogencarbonate, ammonium carbonate, potassium hydroxide, sodium hydroxide, monoethanolamine, ammonium phosphate, sodium citrate, ammonium citrate, sodium lactate, potassium phosphate, and sodium phosphate. From the viewpoint of being weakly alkaline and having a small amount of residue on the hair, as the pH adjusting agent, mention may be made of preferably ammonium hydrogencarbonate, sodium hydrogencarbonate and the like.

From the viewpoint of efficiently opening the cuticle and exhibiting good color retention, the pH value of the hair coloring agent composition of the present invention can be adjusted to preferably pH 3.5 or higher, more preferably pH 5 to 11, and even more preferably pH 6.8 to 10.

Further, in a preferred embodiment of the hair coloring agent composition of the present invention, it is characterized in that the amino acid is at least one selected from cysteine, arginine, lysine, histidine and salts thereof. Further, the amount of amino acids is not particularly limited, but it can be preferably 0.01 to 0.5% by mass, more preferably 0.01 to 0.3% by mass, more preferably 0.02 to 0.2% by mass, based on the total amount of the composition, from the viewpoint of maintaining the moisturizing and softness of the hair.

Further, in a preferred embodiment of the hair coloring agent composition of the present invention, it is characterized in that under the INCI (INCI: International Nomenclature of Cosmetic Ingredient) name, the basic dye is at least one selected from Basic Blue 3, Basic Blue 7, Basic Blue 9, Basic Blue 26, Basic Blue 75, Basic Blue 77, Basic Blue 99, Basic Blue 124, Basic Red 51, Basic Red 76, Basic Yellow 57, Basic Purple 2, Basic Brown 16 or basic brown 17. Moreover, INCI (INCI: International Nomenclature of Cosmetic Ingredient: International Nomenclature of Cosmetic Ingredient) is an international labeling name for cosmetic ingredients created by the International Nomenclature Committee (INC). Further, the amount of the basic dye is not particularly limited, but it can be preferably 0.0005 to 5% by mass, more preferably 0.01 to 3% by mass, even more preferably 0.1 to 1% by mass, based on the total amount of the composition, from the viewpoint that the dyeing power is not strong but the damage to the hair is small.

Further, in a preferred embodiment of the hair coloring agent composition of the present invention, it is characterized in that under the INCI (International Nomenclature of Cosmetic Ingredient) name, the HC dye is at least one selected from HC blue 2, HC blue 12, HC blue 14, HC Blue 15, HC Blue 16, HC Blue 18, HC Yellow 2, HC Yellow 4, HC Yellow 5, HC Red 1, HC Red 3, or HC Orange 1. Moreover, INCI (INCI: International Nomenclature of Cosmetic Ingredient: International Nomenclature of Cosmetic Ingredient) is an international labeling name for cosmetic ingredients created by the International Nomenclature Committee (INC). Further, the amount of the HC dye is not particularly limited, but it can be preferably 0.0005 to 5% by mass, more preferably 0.01 to 3% by mass, and even more preferably 0.1 to 1.5% by mass, with respect to the total amount of the composition, from the viewpoint of exhibiting a deeper color because the HC dye dyes the inside of the hair.

Further, in a preferred embodiment of the hair coloring agent composition of the present invention, it is characterized in that the cationic surfactant is a quaternary ammonium salt and/or a tertiary amine from the viewpoint of further improving the feel given to the hair. Further, in a preferred embodiment of the hair coloring agent composition of the present invention, it is characterized in that the quaternary ammonium salt is an alkyltrimethylammonium chloride solution, stearyltrimethylammonium chloride, or stearyltrimethylammonium bromide. Further, in a preferred embodiment of the hair coloring agent composition of the present invention, it is characterized in that the tertiary amine is dimethylaminopropyl amide stearate, diethyl aminoethyl amide stearate, or behenamide propyl dimethylamine. The amount of the cationic surfactant is not particularly limited, but it can be preferably 0.01 to 10% by mass, more preferably 0.1 to 5% by mass, even more preferably 1 to 3% by mass, based on the total amount of the composition, from the viewpoint of improving the hair dyeing ability of the basic dye.

In addition, the hair coloring agent composition of the present invention may contain a thickener, a wetting agent, an oil agent, and the like. In the present invention, known thickeners and the like can be used without particular limitation as long as the effects of the present invention are not deviated. As the thickener, mention may be made of hydroxyethyl cellulose, xanthan gum, polyethylene glycol and the like from the viewpoint of product stability. Further, the amount of the thickener is not particularly limited, but can be preferably 0.05 to 0.8% by mass, more preferably 0.1 to 0.5% by mass, even more preferably 0.2 to 0.4% by mass, based on the total amount of the composition from the viewpoint of improving the stability of the product.

In addition, as the wetting agent, mention may be made of glycerin, diglycerin, and 1,3-butylene glycol. Further, the amount of the wetting agent is not particularly limited, but is preferably 0.1 to 15% by mass, more preferably 0.5 to 10% by mass, even more preferably 1 to 5% by mass, based on the total amount of the composition, from the viewpoint of ease of application of the product.

Further, as the oil agent, mention may be made of fats and oils, waxes, hydrocarbons, alkylglyceryl ethers, esters, silicones, higher alcohols and the like. Further, the amount of the oil is not particularly limited, but can be preferably 1 to 30% by mass, more preferably 2 to 20% by mass, still more preferably 3 to 15% by mass, from the viewpoint of preventing drying during application leaving time and product stability.

Further, the hair coloring agent of the present invention is characterized by containing the hair coloring agent composition of the present invention. If desired, or depending on the use of the hair coloring agent, the hair coloring agent composition of the present invention can be appropriately included in the hair coloring agent according to the present invention.

Further, in a preferred embodiment of the hair coloring agent composition of the present invention, an antibody production inhibitor can be further contained. As the antibody production inhibitor, mention may be made of pomegranate seed extract, mushrooms belonging to the genus *Agaricus*, and extracts such as yanagihakka and edelweiss from the viewpoint of prevention and improvement of allergic diseases.

For example, the case where pomegranate seed extract is used as an antibody production inhibitor will be described as follows. Pomegranate seed extract is an extract derived from pomegranate seeds. The pomegranate seed extract applied to the present invention covers all pomegranate seed extracts as long as they are derived from pomegranate seeds.

Further, in a preferred embodiment, the pomegranate seed extract is characterized by containing punic acid or ellagic acid. The pomegranate seed extract can be obtained, for example, by the following method. First, it is characterized in that the pulverized product obtained by crushing pomegranate seeds is immersed in at least one solvent selected from the group consisting of ethanol, methanol, water and hexane, and the supernatant is separated to obtain the pomegranate seed extract. For example, it can be shaken and extracted. In the shaking extraction, for example, it can be extracted while being set in a rotator and rotated in a low temperature chamber such as about 4° C.

For more details, first pomegranate seeds are prepared. Pomegranate seeds are washed and dried as needed. It is preferable that the drying is sufficiently performed. This is to perform the subsequent pulverization uniformly.

Next, the pomegranate seeds are crushed. The crushing method is not particularly limited, and a known crusher such as a ball mill, a hammer mill, a roller mill, a rod mill, a sample mill, a stamp mill, a disintegrator, a mortar, and a blender with a cooling device can be used. Moreover, since it is conceivable that the pomegranate seed composition may be decomposed due to heat generated during crushing, the crushing time may be set to several seconds and may be repeated a dozen times.

Next, after crushing the pomegranate seeds to obtain a crushed product, the crushed product is immersed in various solvents. The solvent in this case is not particularly limited, and the solvent can be appropriately set according to the desired effect. Further, in a preferred embodiment of the method for producing a pomegranate seed extract of the present invention, it is characterized in that the solvent is at least one selected from the group consisting of ethanol, methanol, hexane and water. As the solvent, mention may be made of polar and non-polar solvents such as ethanol, methanol, water, hexane, ethyl acetate, chloroform and acetone. Preferably, methanol, ethanol, water and the like can be mentioned.

Immersion can be performed under gentle stirring. The pulverized product is immersed in various solvents to obtain various solutions. The various solutions may be stirred according to the state of the solution, and the solution may be left as it is in some cases. In the case of stirring, the stirring is not particularly limited, but the stirring can be continued for 10 hours to 48 hours, preferably about 1 day (24 hours).

After that, the pomegranate seed extract can be obtained by separating the supernatant. If necessary, the supernatant is evaporated to dryness. Evaporation to dryness can be carried out using an evaporator on a warm bath at 20° C. to 60° C., preferably 37° C. to 40° C. By evaporating to dryness, the pomegranate seed extract can be stored for a long period of time.

The components contained in the pomegranate seeds are sorted according to their physical characteristics by extracting the pomegranate seeds with solvents having different polarities. Therefore, the type and content of the components of the pomegranate seed extract differ depending on the solvent used.

Moreover, in the present invention, an example of the hair coloring method will be described below.

1) Pre-shampoo as appropriate is carried out to remove hair styling products and stains.

2) Hair coloring agent (containing hair dye component) and hair cosmetic (containing basic cuticle swelling agent) applicable to the present invention were mixed in a predetermined ratio, and a mixture is applied to the hair by a brush.

3) The applied hair is covered with plastic wrap to heat it with a hair dryer or heat cap, and to leave it for about 30 minutes.

4) After 3), if necessary, the cuticle care agent is sufficiently applied to the hair and to leave it for about 6 minutes.

5) After 4), your hair is washed with hot water and shampoo.

6) After towel drying, the hair is dried with a hair dryer.

EXAMPLE

An embodiment of the present invention will be described below, but the present invention is not construed as being limited to the following examples.

Example 1

Regarding the alkaline agent (pH adjuster), from the viewpoint of being weakly alkaline and less likely to cause skin irritation, in this example, a test was conducted using ammonium hydrogen carbonate as an example.

In addition, about 80% of human hair is composed of keratin protein derived from amino acids, L-cysteine is an amino acid that is also abundant in the hair. Therefore, L-Cysteine and its salts were tried to be formulated for the purpose of keeping the hair moisturized and soft. Typical basic amino acids include L-arginine, L-lysine, and L-histidine, but these are known to flow out when damaged, and it was found to be preferable 0.01 to 0.5% by mass of basic amino acids and salts thereof.

Table 1 shows component examples of the hair coloring agent composition according to one embodiment of the present invention.

TABLE 1

| | Abbreviation or Product name | Components (Display name) | Manufacturer | Compounding amount (% by mass) |
|---|---|---|---|---|
| Water phase | Water | Water | | Residue |
| | Concentrated glycerin for cosmetic | Glycerin | Sakamoto Pharmaceutical Co., Ltd. | 1.00 |
| | 1,3-butylene glycol-P | BG | KH Neochem Co. Ltd. | 1.00 |
| | | Pentylene glycol | | 1.00 |
| | | Hydroxyethyl cellulose | | 0.25 |
| | | Thioglycerin | Asahi Kagaku Kogyo Co., Ltd. | 0.10 |
| | Catinal STB-70 | Steartrimonium bromide | Toho Chemical Industry Co., Ltd. | 1.50 |
| | | Isopropanol | | 1.00 |
| Oil phase | KALCOL 4098 | Myristyl alcohol | Kao Corporation | 5.00 |
| | Lanette 22 | Behenyl alcohol | BASF Japan Co., Ltd. | 1.00 |
| | Cegesoft C24 | Ethylhexyl palmitate | BASF Japan Co., Ltd. | 2.00 |
| | Cutina CP | Cetyl palmitate | BASF Japan Co., Ltd. | 1.00 |
| | | Glycol stearate | | 2.00 |
| | Refined shea butter | Shea fat | Koei Kogyo Co., Ltd. | 1.00 |
| Alkaline agent | | Ammonium hydrogen carbonate | | 1.00 |
| Emulsification stable/viscosity imparting ingredient | Hisolve EPH | Phenoxyethanol | Toho Chemical Industry Co., Ltd. | 0.60 |
| | L-Menthol | Menthol | K. Kobayashi & Co., Ltd. | 0.10 |
| | Dehydrated ethanol | Ethanol | Kenei Pharmaceutical Co., Ltd. | 1.00 |
| Anti-inflammatory ingredient | Dipotassium glycyrrhizinate | Glycyrrhizic acid 2K | Maruzen Pharmaceutical Co., Ltd. | 0.10 |
| Antiallergic ingredient | Pomegranate seed extract BG-100 | Pomegranate seed extract | Koei Kogyo Co., Ltd. | 0.50 |
| Pigment | | Basic blue 99 | | 0.30 |
| | | Basic brown 16 | | 0.50 |
| | | HC blue 2 | | 0.60 |
| | | HC yellow 4 | | 0.20 |
| | | HC yellow 2 | | 0.10 |

TABLE 1-continued

| | Abbreviation or Product name | Components (Display name) | Manufacturer | Compounding amount (% by mass) |
|---|---|---|---|---|
| Amino acid group | L-Arginine | Arginine | Kyowa Hakko Bio Co., Ltd. | 0.10 |
| | L-histidine hydrochloride monohydrate | Histidine HCl | Wako Pure Chemical Industries, Ltd. | 0.02 |
| | L-lysine hydrochloride | Lysine HCl | Wako Pure Chemical Industries, Ltd. | 0.02 |
| | Tolat (% by mass) | | | 100.00 |
| | pH | | | 8.00 |

The preparation method is as follows.

Preparation Method:

1. The aqueous phase (water phase) of Table 1 is warmed to 75-77° C. with stirring.
2. The oil phase in Table 1 is stirred while heating to 77-79° C. to make it uniform.
3. The pigment is added to water phase heated to 75-77° C. to homogenize, the oil phase is add to the mixture to emulsify and stir until uniform.
4. The content is slowly cooled, and when the temperature of the content is 43° C. or lower, the preservative, the refreshing component, the antiinflamator component, and the amino acid group are added and stirred until uniform, and then cooled to 32° C. or lower.

Moreover, the following models and electrodes were used for pH measurement.

Model of pH meter: F-71 (Horiba, Ltd.) pH meter electrode: Type 9615 (Horiba, Ltd.)

In addition, a hair colorant of the present invention was prepared, and a color fading test was performed on the hair bundle. As a result, it was found that the hair coloring agent of the present invention was extremely excellent in color fading.

Conventionally, when a hair coloring agent that does not contain paraphenylenediamine is applied and left as it is, although, the base color is a basic dye and HC dye, which are considered to be safer than oxidative dyes, since it was dyed on the hair, the color persistence after the hair dyeing was bad, and there was the fault that it was easy to lose color due to repeated shampooing. It was found that in contrast to conventional hair coloring agents, the hair coloring agent of the present invention not only the base color easily penetrates but also it can be applied from the new part to the hair tip without worrying about adhesion to the scalp because it does not contain an acidic dye.

Thus, in the hair coloring agent etc., of the present invention, when performing hair dye, compared with conventional hair color and hair manicure, in the conventional method, there are problems that 1) if the hair is damaged by repeated dyeing, the hair strength is reduced and elasticity is lost to thin a hair (In the case of hair color of prior art), 2) if the scalp rash occurs, the rash part will stain and be difficult to remove (in the case of hair manicure of prior art). However, in the present invention, there is no problem of the above, it was found that hair cosmetics with good penetration and dyeing power can be provided. In other words, in the present invention, it has also been found that safety is provided in addition to color retention.

Example 2

The penetration of major basic dyes applicable to the present invention was compared. A hair commercially available 100% untreated gray hair (product number: BS-C, manufactured by Burax Co., Ltd.) with a length of 30 cm was divided into three equal parts to obtain a hair sample to be dyed. For Basic Red 51, Basic Brown 16 and 17, 0.2% of the pigment was dissolved in purified water, and the pH was adjusted to alkaline using 25% of ammonia water (manufactured by Wako Pure Chemical Industries, Ltd.), and a 0%, 1% and 3% solution of 3-mercapto-1,2-propanediol (manufactured by Wako Pure Chemical Industries, Ltd.) as thioglycerin was prepared. The optimum value of alkalinity is around pH 7.5 to 10.0, but there are differences depending on the dye, and some dyes cause precipitation in the solution if the pH is raised too much. In addition, for Basic Blue 75, 77, 99, Basic Violet 2, and Basic Yellow 57, 0.7% of dye was dissolved in 5.0% of amide betaine type amphoteric tenside coconut oil fatty acid amide propyl betaine solution (product number: softazoline CPB-R, Kawaken Fine Chemicals Co., Ltd.) to improve dye solubility, and was dissolved in purified water, and the pH was adjusted to alkaline using 25% of ammonia water (manufactured by Wako Pure Chemical Industries, Ltd.), and a 0%, 1% and 3% solution of 3-mercapto-1,2-propanediol (manufactured by Wako Pure Chemical Industries, Ltd.) was prepared. A hair sample obtained by dividing one gray hair into three equal parts is dipped in a 0%, 1%, 3% solution of 3-mercapto-1,2-propanediol of each dye, and left for 30 minutes in a constant temperature bath at 40° C. to obtain a stained hair sample. The hair sample was freeze-embedded with PVA resin, and then a hair cross-section sample (section thickness: 10 μm) was prepared using a microtome. Then, they were placed on a slide glass as a sample for microscopic observation and compared with a microscope (FIG. 1).

As shown in FIG. 1, it is found that the degree of penetration of the dye into the hair sample is deepest in all the dyes in the case of 3% of 3-mercapto-1,2-propanediol (the range where the color is dark from the outer periphery of the cross section is the largest one). In particular, it was more clear that the dyes of Basic Brown 16 and Basic Blue 77 had good penetration.

Example 3

Using the dyes of Basic Brown 16 and Basic Blue 77, which had good penetration in Example 2, a hair commercially available 100% untreated gray hair (product number: BS-C, manufactured by Beaulax Co., Ltd) was left for 30 minutes in a constant temperature bath at 40° C. and the hair was dyed dark brown in the following formulation example (Table 2). Table 2 shows examples of ingredients and formulations at this time. The hair sample was freeze-embedded with PVA resin, and then a hair cross-section sample (section thickness: 10 μm) was prepared using a microtome. Then, they were placed on a slide glass as a sample for microscopic observation and compared with a microscope (FIG. 2).

TABLE 2

| Components | Formulation | | | |
|---|---|---|---|---|
| | a) | b) | c) | d) |
| Purified water | Amount to be 100 in total | | | |
| 3-mercapto-1,2-propanediol | 0 | 0.5 | 1 | 3 |
| Coconut oil fatty acid amide propyl betaine solution | 5 | 5 | 5 | 5 |
| Basic Brown 16 | 0.2 | 0.2 | 0.2 | 0.2 |
| Basic Blue 77 | 0.2 | 0.2 | 0.2 | 0.2 |
| 25% of ammonia water | q.s. | q.s. | q.s. | q.s. |
| pH | 10.403 | 9.874 | 9.461 | 8.994 |

Example 4

A hair commercially available 100% untreated gray hair (product number: BM-W-A, manufactured by Burax Co., Ltd.) with a weight of 1 g and a length of 10 cm was dyed using the formulation of Example 1, and the hair bundle was washed with the following washing liquid for 5 minutes using a desktop type of ultrasonic cleaner. An amino acid-based anionic surfactant N-coconut oil fatty acid acyl-L-glutamic acid triethanolamine solution (product number: Amino Surfact ACMT-L, manufactured by Asahi Kasei Finechem Co., Ltd.) was used as the cleaning solution. Table 3 shows the components of the cleaning solution.

TABLE 3

| Components | % |
|---|---|
| Purified water | 98 |
| N-coconut oil fatty acid acyl-L-glutamic acid triethanolamine solution | 1.5 |
| Phenoxyethanol | 0.5 |

TABLE 4

| Prescription | Number of washing | L* | a* | b* |
|---|---|---|---|---|
| 3-mercapto-1,2-propanediol 0% formulation of Example 3 a) | 0 | 21.12 | 8.02 | 5.5 |
| | 10 | 29.52 | 11.28 | 9.26 |
| | 20 | 36.11 | 11.79 | 10.56 |
| 3-mercapto-1,2-propanediol 0.5% formulation of Example 3 b) | 0 | 19.23 | 3.06 | 2.94 |
| | 10 | 24.13 | 7.3 | 6.17 |
| | 20 | 25.35 | 5.75 | 4.83 |
| 3-mercapto-1,2-propanediol 1.0% formulation of Example 3 c) | 0 | 18.20 | 2.16 | 1.3 |
| | 10 | 22.07 | 3.67 | 4.56 |
| | 20 | 24.19 | 7.46 | 5.42 |
| 3-mercapto-1,2-propanediol 3.0% formulation of Example 3 d) | 0 | 17.66 | 0.9 | 1.23 |
| | 10 | 20.01 | 0.82 | −0.28 |
| | 20 | 19.15 | 1.5 | −0.69 |

Next, in order to quantify the color fading due to the number of times wherein the hair was washed, it was measured with a spectroscopic colorimeter (manufactured by Nippon Denshoku Industries Co., Ltd., device name: SD6000). Table 4 shows the colors (L *, a *, b *) of the number of washings of each formulation. Table 4 shows the results regarding discoloration due to the number of times wherein the hair was washed. The difference in color due to the number of times wherein the hair was washed was measured using lightness (L *) or the like. In Table 4, it is shown that L * is the brightness, and light and dark colors are quantified, and the smaller the value, the darker the color. It is shown that a * indicates that the larger the value, the more red the direction, and the smaller the value, the greener the direction. In addition, it is shown that b * indicates that if the value is large, it advances in the yellow direction, and if the value is small, it advances in the blue direction.

Therefore, when thioglycerin is 0%, it is recognized that the values of L *, a * and b * are increased by washing 20 times, so the blackness is reduced and the red and yellow are stronger, so the color is closer to brown. On the contrary, in the case of 3%, the values of L *, a *, and b * hardly move, indicating that there is almost no change even after 20 washes. Moreover, the closer the value of L * is to 0, the darker the value. From these results, it can be seen that according to the present invention, there is little decrease in lightness and very little discoloration due to washing hair.

Example 5

Using the dyes of Basic Brown 16 and Basic Blue 77, which had good penetration in Example 2, a hair commercially available 100% untreated gray hair (product number: BS-C, manufactured by Beaulax Co., Ltd) was left for 30 minutes in a constant temperature bath at 40° C. and the hair was dyed dark brown in the following formulation example (Table 5). Table 5 shows examples of ingredients and formulations at this time. The hair sample was freeze-embedded with PVA resin, and then a hair cross-section sample (section thickness: 10 μm) was prepared using a microtome. Then, they were placed on a slide glass as a sample for microscopic observation and compared with a microscope (FIG. 3). FIG. 3 shows the observation result by the optical microscope of the hair cross-section sample treated in 0%, 0.5%, 1%, 3%, 4% 5% and 10% solutions of 3-mercapto-1,2-propanediol when 0.2% of Basic Brown 16 and 0.2% of Basic Blue 77 were mixed to make a dark brown color.

TABLE 5

| Components | Formulation of Example 2 | | |
|---|---|---|---|
| | e) | f) | g) |
| Purified water | Amount to be 100 in total | | |
| 3-mercapto-1,2-propanediol | 4 | 5 | 10 |
| Coconut oil fatty acid amide propyl betaine solution | 5 | 5 | 5 |
| Basic Brown 16 | 0.2 | 0.2 | 0.2 |
| Basic Blue 77 | 0.2 | 0.2 | 0.2 |
| 25% of ammonia water | q.s. | q.s. | q.s. |
| pH | 8.792 | 8.759 | 8.474 |

From the above results, it was found that when thioglycerin or the like is blended, it is possible to dye hair having good robust characteristics without raising the pH or heating. Moreover, it was also found that it is more effective to add thioglycerin or the like and to increase the heating and pH. It was found that in the case of the dyes Basic Blue 99 and Basic brown 16, it is possible to dye hair with better robustness as the pH is raised to around pH 10, while in the case of Basic Blue 77, as the pH is raised to pH 8 or higher, the pigment broke and the color changed, resulting in weak hair dyeing.

From the above, it was found that the addition of thioglycerin makes it easier for dyes to enter the hair when coloring hair.

INDUSTRIAL APPLICABILITY

According to the present invention, a coloring method that does not easily damage hair, can reduce skin disorders, and allows dyes to easily enter hair is easy to spread and has high industrial utility value.

The invention claimed is:

1. A hair coloring agent composition comprising:
a basic dye, an HC dye, an amino acid, a cationic surfactant, a thickener, an oil agent, a pH adjusting agent, a wetting agent; and
at least one selected from the group consisting of thioglycolic acid, 3-mercapto-1, 2-propanediol, cysteamine, and derivatives and salts thereof,
wherein
the pH of the hair coloring agent composition is in a range between pH 6.8 and pH 10, and
the pH adjusting agent comprises ammonium hydrogencarbonate or sodium hydrogencarbonate.

2. The hair coloring agent composition according to claim 1, wherein the pH adjusting agent further comprises at least one selected from citric acid, phosphoric acid, lactic acid, malic acid, aqueous ammonia, ammonium carbonate, potassium hydroxide, sodium hydroxide, monoethanolamine, ammonium phosphate, sodium citrate, ammonium citrate, sodium lactate, potassium phosphate, or sodium phosphate.

3. The hair coloring agent composition according to claim 1, wherein the amino acid is at least one selected from cysteine, arginine, lysine, histidine, or salts thereof.

4. The hair coloring agent composition according to claim 1, wherein under the INCI (INCI: International Nomenclature of Cosmetic Ingredient) name, the basic dye is at least one selected from Basic Blue 3, Basic Blue 7, Basic Blue 9, Basic Blue 26, Basic Blue 75, Basic Blue 77, Basic Blue 99, Basic Blue 124, Basic Red 51, Basic Red 76, Basic Yellow 57, Basic Purple 2, Basic Brown 16, or Basic Brown 17.

5. The hair coloring agent composition according to claim 1, wherein under the INCI (International Nomenclature of Cosmetic Ingredient) name, the HC dye is at least one selected from HC blue 2, HC blue 12, HC blue 14, HC Blue 15, HC Blue 16, HC Blue 18, HC Yellow 2, HC Yellow 4, HC Yellow 5, HC Red 1, HC Red 3, or HC Orange 1.

6. The hair coloring agent composition according to claim 1, wherein the cationic surfactant is at least one of a quaternary ammonium salt or a tertiary amine.

7. The hair coloring agent composition according to claim 6, wherein the quaternary ammonium salt is an alkyltrimethylammonium chloride solution or stearyltrimethylammonium bromide.

8. The hair coloring agent composition according to claim 6, wherein the tertiary amine is dimethylaminopropyl amide stearate, diethyl aminoethyl amide stearate, or behenamide propyl dimethylamine.

* * * * *